United States Patent [19]
Lebwohl et al.

[11] Patent Number: 6,048,902
[45] Date of Patent: Apr. 11, 2000

[54] SHORT CONTACT TREATMENT OF PSORIASIS WITH TOPICAL RETINOIDS

[76] Inventors: Mark G. Lebwohl, 300 E. 85th St., New York, N.Y. 10028; Susan Bershad, 2 Stonebridge Rd., Montclair, N.J. 07042

[21] Appl. No.: 09/249,386

[22] Filed: Feb. 12, 1999

[51] Int. Cl.$^7$ ........................................... A61K 1/04
[52] U.S. Cl. ................................................. 514/725
[58] Field of Search ...................... 514/474, 725; 435/6

[56] References Cited

U.S. PATENT DOCUMENTS

| | | |
|---|---|---|
| 5,089,509 | 2/1992 | Chandraratna . |
| 5,516,793 | 5/1996 | Duffy ........................................ 514/474 |
| 5,650,279 | 7/1997 | Nagpal et al. ............................. 435/6 |
| 5,719,195 | 2/1998 | Braiman .................................... 514/725 |
| 5,776,687 | 7/1998 | Nagpal et al. ............................. 435/6 |

OTHER PUBLICATIONS

Leyden, James J., Emerging Topical Retinoid Therapies, Journal of the American Academy of Dermatology, Apr. 1998, vol. 38, No. 4, pp. S1–S4.

Chandraratna, R., Tazarotene—first of a new generation of receptor–selective retinoids, British Journal of Dermatology 1996, vol. 135, pp. 18–25.

Azelex package insert by Allegan(manufacture), N/A.

Retin–A package insert by Ortho–Derm(manufacture), N/A.

Allergan Tazorac Plaque psoriasis . . . , Tpink sheet: FDC report, vol. 59/25, Jun. 1997.

Tazorac package insert by allergan(manufacture), N/A.

Lavker et al., An Ultrastructural study of the effects of topical tretinoin . . . , vol. 14(6), pp. 773–780, 1992.

*Primary Examiner*—Keith D. MacMillan
*Assistant Examiner*—Vickie Kim
*Attorney, Agent, or Firm*—Kenyon & Kenyon

[57] ABSTRACT

The present invention relates to a method of treating psoriasis using short-term contact with a topically-applied retinoid composition.

12 Claims, No Drawings

SHORT CONTACT TREATMENT OF PSORIASIS WITH TOPICAL RETINOIDS

BACKGROUND OF THE INVENTION

The present invention is directed to the treatment of psoriasis using topical retinoids.

The retinoids are a family of compounds including vitamin A, retinoic acid (RA), related derivatives of these, and other compounds capable of binding to retinoic acid receptors (RAR). RA, which is a natural metabolite of vitamin A (retinol), is known as a potent modulator (i.e., an inhibitor or, to the contrary, a stimulator, depending on the nature of the cells treated) of the differentiation and proliferation of many normal or transformed cell types. All-trans-RA (tretinoin) acts on the differentiation and proliferation of cells by interacting with RARs contained in the cell nucleus. There are, to date, three identified subtypes of known RAR receptors, respectively termed RAR-$\alpha$, -$\beta$, -$\gamma$. These receptors, after binding the RA ligand. interact with the promoter region of genes regulated by RA at specific response elements. To bind to the response elements, the RARs heterodimerize with another type of receptor designated as RXR. The natural ligand of RXRs is 9-cis-retinoic acid.

Many retinoids are known and have been described to date. Generally, retinoids can be identified by their ability to bind RARs, either as all the RARs or selectively to an individual RAR class. Further, retinoids exhibit a diverse spectrum of activities. Among these is use as a topical therapeutic for treatment of skin conditions.

There is presently in use an FDA approved treatment for psoriasis employing tazarotene topical gel that is marketed by Allergan, Inc. under the brand name Tazorac™. Moreover, tretinoin, also known by the tradename Retin-A™, and adapalene are approved for topical use to treat skin conditions.

The mechanism of action in the treatment of psoriasis with tazarotene or other retinoids is not known. The current FDA-approved therapeutic regimen requires Tazorac™ gel to be applied topically in its 0.05% or its 0.1% formulation and left on the affected skin for long periods of time, e.g. overnight. It is generally applied in the evening and left in place until routine washing in the morning. Thus, in the treatment of psoriasis, the Tazorac™ gel would typically be left on the skin for 8 to 12 hours.

Unfortunately, a major shortcoming of this course of treatment is that adverse skin reactions are experienced by a significant portion of users. These reactions include pruritus, burning/stinging and erythema (sometimes severe), actual worsening of psoriasis, irritation and skin pain. Since the treatment regimen is usually prolonged, covering many weeks or months, any adverse reactions are rendered even more substantial in the perception of the user, often resulting in the interruption or abandonment of the treatment regimen. Thus the adverse reactions are not merely significant in-and-of themselves, but can make treatment ineffectual due to the inability or unwillingness of the user to follow the regimen.

To overcome these shortcomings, it has now been found that topically-applied retinoids can be used to treat psoriasis using a short-contact treatment regimen. For example. tazarotene has been used for short-contact therapy to treat psoriasis as disclosed in co-pending application entitled "Short Contact Treatment of Psoriasis with Tazarotene Compositions," filed on the same day as this application by the same inventors and which is hereby incorporated herein by reference.

SUMMARY OF THE INVENTION

The present invention is directed to a method of treating psoriasis in a human patient by topically applying an effective amount of a retinoid composition to the affected area of a patient's skin, allowing that composition to remain in contact with the skin for a period of from about thirty seconds to about thirty minutes, followed by rinsing the composition from the affected area. Generally, the short contact treatment is performed once a day at least three times a week as long as treatment is needed. In preferred embodiments, the active retinoid in the composition is tazarotene, tretinoin or adapalene and. more preferably, is tazarotene.

DESCRIPTION OF THE INVENTION

According to the invention, it has been found that short-contact retinoid therapy yields surprisingly improved and beneficial results in the treatment of psoriasis.

"Short-contact retinoid therapy", as used herein, is intended to distinguish over conventional, or extended-contact, treatment(s) the retinoid of interest is applied to a patient's skin (typically once a day) and left on the skin indefinitely or until routine washing or showering occurs after a prolonged period of time (typically overnight).

In accordance with the invention, short-contact retinoid therapy thus comprises the steps of applying a retinoid composition to an affected area of the skin for a brief time period followed by rinsing of the skin/affected area. For psoriasis, the usual contact time is from about 30 seconds to about 30 minutes, preferably for a period of from about 5 to about 10 minutes. Immediately following the prescribed period of time, the skin is rinsed thoroughly, typically with lukewarm water.

For psoriasis therapy, the short-contact treatments are generally applied to the affected area(s) once or twice a day, preferably once a day, and repeated at least three times a week. If desired or needed, the treatments can be repeated daily. The overall duration of therapy is continued for as long as the conditions exist, i.e., until the plaques are gone or have disappeared, and can readily be determined by the patient's doctor.

In accordance with the invention and as used herein, a "retinoid composition" comprises therapeutically-active retinoids, or pharmaceutically-acceptable salts thereof, in admixture with a pharmaceutically acceptable carrier. The therapeutically-active retinoids of the invention are selected from the group consisting of a retinoic acid; retinol; therapeutically-active retinoic acid derivatives; therapeutically-active carboxylic acids represented by the formula

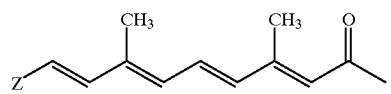

and retinoids which are C20 or C22 desmethyl vinylogs of said groups, wherein Z is a substituted or unsubstituted phenyl group, a substituted or unsubstituted naphthyl group or a cyclohexenyl group, and said phenyl or naphthyl group can be substituted with from 0 to 5 substitutents selected from the group consisting of halo, hydroxy, alkly, alkyoxy, amino, cyano or carbalkoxy, and wherein double bonds in the polyene chain of any of said groups can have a cis or trans configuration; acetylenic retinoids; adapalene; adapalene derivatives and any compound, natural or synthetic, which possesses the topical biological activity of retinoic acid in the skin and/or the ability to bind to one or more RARs; as well as the geometric isomers and steriosomers of any of these compounds.

Examples of retinoids contemplated by the invention can be found in U.S. Pat. Nos. 4,476,056; 4,105,681; 4,215,215; 4,054,589 and 3,882,244. Retinoids include both cis and trans forms having therapeutic activity. The retinoids can include a 9-cis double bond, a 13-cis double bond or a 13-trans double bond. Derivatives of retinoic acid include, but are not limited to, esters, amides, other biologically active forms of retinoic acid such as those with a chemical modification or substitution of a substituent of the molecule, and the like. Derivatives of adapalene include, but are not limited to, esters and amides of the naphthoic acid moiety, other biologically active forms of adapalene such as those having a chemical modification or substitution on some part of the molecule while retaining activity. and the like.

A pharmaceutically acceptable salt may be prepared for any compound of this invention having a functionality capable of forming such salt, for example an acid or amine functionality. A pharmaceutically acceptable salt may be any salt which retains the activity of the parent compound and does not impart any deleterious or untoward effect on the subject to which it is administered and in the context in which it is administered.

The preferred compounds of the invention include, but are not limited to, retinoic acid including tretinoin, 13-cis retinoic acid, 9-cis-retinoic acid, acetylenic retinoids including tazarotene and adapalene.

As used herein a "therapeutically-active retinoid" is a compound which, when applied topically, exhibits or possesses a biological action similar to retinoic acid (i.e., similar to vitamin A acid). Hence, these retinoids include those compounds, synthetic or natural, which have one or more of the therapeutic activities known for retinoic acid. Such activities include but are not limited to binding to and activating RARs, treating and preventing cancer and other proliferative disorders, acting as differentiating agents or anti-proliferatives agents and anti-tumor activity.

As used herein "vinylogs" are desmethyl retinoyl groups having 1 or 2 additional vinyl groups relative to retinoic acid. For example such compounds include 2,6,6-trimethyl-1-(10'-carboxy-deca-1',3',5',7',9'-pentaenyl)cyclohex-1-ene and 2,6,6-trimethyl-1-(12'-carboxy-dodeca-1',3',5',7',9',11'-hexaenyl)cyclohex-1-ene. These groups are also referred to as C20 and C22 vinylogs of desmethyl retinoic acid and are described in U.S. Pat. No. 3,882,244. The vinylogs of this invention can be prepared from a retinoyl group, any therapeutically active retinoid carboxyl group, or any group of the formula

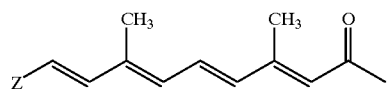

wherein Z is as defined herein.

The acetylenic retinoids of the invention are the compounds of the formula represented by

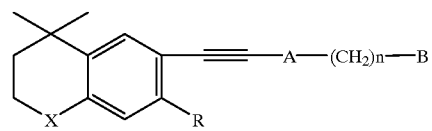

wherein X is S, O, or NR' where R' is hydrogen or lower alkyl; R is hydrogen or lower alkyl; A is pyridinyl, thienyl, furyl, pyridazinyl, pyrimidinyl or pyrazinyl; n is 0–2; and B is H, —COOH or a pharmaceutically acceptable salt, ester or amide thereof, —CH$_2$OH or an ether or ester derivative, or —CHO or an acetal derivative, or —COR$_1$ or a ketal derivative where R$_1$ is —(CH$_2$)$_m$CH$_3$ where m is 0–4.

The term "ester" as used here refers to and covers any compound falling within the definition of that term as classically used in organic chemistry. Where A is —COOH, this term covers the products derived from treatment of this function with alcohols. Where the ester is derived from compounds where A is —CH$_2$OH, this term covers compounds of the formula —CH$_2$OOCR where R is any substituted or unsubstituted aliphatic, aromatic or aliphatic-aromatic group.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Here, and where ever else used, lower alkyl means having 1–6 carbon atoms. Also preferred are the phenyl or lower alkylphenyl esters.

The term "amide" has the meaning generally accorded that term in organic chemistry. In this instance it includes the unsubstituted amides and all aliphatic and aromatic mono- and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from lower alkyl amines. Also preferred are mono- and di-substituted amides derived from the phenyl or lower alkylphenyl amines. Unsubstituted amides are also preferred.

Acetals and ketals includes the radicals of the formula —CK where K is (—OR)$_2$. Here, R is lower alkyl. Also, K may be —OR$_1$O— where R$_1$ is lower alkyl of 2–5 carbon atoms, straight chain or branched.

The preferred acetylenic retinoid compounds of this invention are those where the ethynyl group and the B group are attached to the 2 and 5 positions respectively of a pyridine ring (the 6 and 3 positions in the nicotinic acid nomenclature being equivalent to the ⅖ designation in the pyridine nomenclature) or the 5 and 2 positions respectively of a thiophene group respectively; n is 0; and B is —COOH, an alkali metal salt or organic amine salt, or a lower alkyl ester, or —CH$_2$OH and the lower alkyl esters and ethers thereof, or —CHO and acetal derivatives thereof.

The preferred compounds include:
ethyl 6-(2-(4,4-dimethylthiochroman-6-yl)ethynyl)-nicotinate;
6-(2-(4,4-dimethylthiochroman-6-yl)ethynyl)nicotinic acid;
ethyl 6-(2-(4,4-dimethylchroman-6-yl)ethynyl)nicotinate;
ethyl 6-(2-(4,4,7-trimethylthiochroman-6-yl)ethynyl)-nicotinate;
ethyl 6-(2-(4,4-dimethyl-1,2,3,4-tetrahydroquinolin-6-yl)ethynyl)nicotinate;
ethyl 5-(2-(4,4-dimethylthiochroman-6-yl)ethynyl)thiophene-2-carboxylate;

6-(2-4,4-dimethylthiochroman-6-yl)-ethynyl)-3-pyridylmethanol; and
2-(2-(4,4-dimethylthiochroman-6-yl)-ethynyl)-5-pyridinecarboxaldehyde.

The compounds of the invention can be purchased or made by methods known in the art. One means to make such compounds is provided in U.S. Pat. No. 5,089,509 which is hereby incorporated herein by reference.

The "retinoid composition" contains the retinoid compounds of the invention in amounts suitable for topical use on humans. Such compositions may be in the form of a gel, cream lotion, ointment, cleanser or solution and include a variety of preservatives, carriers and other inactive or active ingredients.

As used herein, "therapeutically-effective amount" refers to that amount of a therapeutically-active retinoid necessary to administer to a human patient to treat psoriasis. Such amounts depend on the retinoid and its bioavailability but can range from about 0.01% to about 10% by weight, or preferably from about 0.025% to about 1–5% by weight. For tazarotene, commercially available preparations of 0.05% and 0.1% are effective. Therapeutically-effective amounts can be readily determined by one of ordinary skill in the art.

As demonstrated by the following examples, surprisingly good results are obtainable using short-contact retinoid therapy. Not only does it appear that there is no loss of effectiveness of the active retinoid ingredient (as compared with conventional extended-contact therapy), but also that the effectiveness may be enhanced in some instances. Even more important, the adverse reactions are substantially reduced to tolerable or even negligible levels, thereby resulting in the ability and willingness of the user to adhere to the novel regimen. This combination of effects, i.e., equal or enhanced effectiveness, reduction in adverse reactions, and regimen adherence, yields surprisingly improved therapeutic efficacy.

EXAMPLE 1

Three patients were treated for psoriasis with short-contact tazarotene therapy for a period of at least six weeks. The contact period was from 30 seconds to 30 minutes followed by immediate rinsing. All three patients showed greater than 75% reduction in plaque thickness and scale. These results were significantly better thatn those seen in corresponding plaques which were either untreated (one patient) or treated with traditional phototherapy (two patients). One of 3 patients noted minor irritation.

Short-contact tazarotene therapy for psoriasis has also been used successfully on alternate-day and three-times-weekly schedules.

We claim:

1. A method of treating psoriasis in a human patient comprising the steps of (1) topically applying an effective amount of a retinoid composition to the affected area of a patient's skin; (2) allowing said composition to remain in contact with the skin for a period of from about thirty seconds to about thirty minutes; and (3) rinsing said retinoid composition from said affected area.

2. The method according to claim 1 wherein said composition remains in contact with the skin for a period of from about two to about ten minutes.

3. The method according to claim 1 wherein said retinoid composition comprises tretinoin, tazarotene or adapalene as the topically active retinoid.

4. The method according to claim 2 wherein said retinoid composition comprises tretinoin tazarotene or adapalene as the topically-active retinoid.

5. The method according to claim 3 wherein said topically-active retinoid is present in an amount of about 0.01% to about 10% by weight.

6. The method according to claim 4 wherein said topically-active retinoid is present in an amount of about 0.01% to about 10% by weight.

7. The method according to any one of claims 1–6, wherein steps (1) to (3) are carried out at least 3 times per week.

8. The method according to claim 1, wherein said retinoid composition comprises tazarotene as a topically-active retinoid.

9. The method according to claim 2, wherein said retinoid composition comprises tazarotene as a topically-active retinoid.

10. The method according to claim 8, wherein said topically-active retinoid is present in an amount of about 0.01% to about 10% by weight.

11. The method according to claim 9, wherein said topically-active retinoid is present in an amount of about 0.01% to about 10% by weight.

12. The method according to any one of claims 8–11 wherein steps (1) to (3) are carried out at least 3 times per week.

* * * * *